(12) United States Patent
Park

(10) Patent No.: US 12,064,096 B2
(45) Date of Patent: Aug. 20, 2024

(54) NEEDLE GUIDE DEVICE FOR BIOPSY

(71) Applicant: MEDICAL PARK CO., LTD., Yongin-si (KR)

(72) Inventor: Hee Boong Park, Seoul (KR)

(73) Assignee: MEDICAL PARK CO., LTD., Yongin-si (KR)

( * ) Notice: Subject to any disclaimer, the term of this patent is extended or adjusted under 35 U.S.C. 154(b) by 900 days.

(21) Appl. No.: 17/137,376

(22) Filed: Dec. 30, 2020

(65) Prior Publication Data

US 2022/0202400 A1    Jun. 30, 2022

(51) Int. Cl.
*A61B 5/00* (2006.01)
*A61B 10/02* (2006.01)
*A61B 17/34* (2006.01)

(52) U.S. Cl.
CPC ...... *A61B 10/0233* (2013.01); *A61B 17/3403* (2013.01); *A61B 2010/0208* (2013.01); *A61B 2017/3409* (2013.01); *A61B 2017/3411* (2013.01)

(58) Field of Classification Search
CPC ............ A61B 10/0233; A61B 17/3403; A61B 2010/0208; A61B 2017/3409; A61B 2017/3411; A61B 2090/062
See application file for complete search history.

(56) References Cited

U.S. PATENT DOCUMENTS

| 5,236,334 | A | 8/1993 | Bennett |
| 5,810,806 | A * | 9/1998 | Ritchart ............. A61B 10/0266 606/41 |
| 7,419,472 | B2 | 9/2008 | Hibner |
| 7,883,476 | B2 * | 2/2011 | Miller .................. A61B 10/025 600/587 |
| 8,177,728 | B2 | 5/2012 | Hibner |
| 8,206,316 | B2 | 6/2012 | Hibner |
| D737,440 | S * | 8/2015 | Shabaz ........................ D24/146 |
| 11,185,344 | B2 * | 11/2021 | Langhals ............ A61B 17/3205 |
| 11,607,205 | B2 * | 3/2023 | Larson ................ A61B 10/0275 |
| 2004/0122373 | A1 | 6/2004 | Botich et al. |
| 2005/0054948 | A1 * | 3/2005 | Goldenberg ......... A61B 10/025 600/567 |
| 2005/0277845 | A1 * | 12/2005 | Cooke ................ A61B 10/0275 600/564 |
| 2008/0004545 | A1 * | 1/2008 | Garrison ............ A61B 10/0096 600/566 |
| 2008/0269638 | A1 * | 10/2008 | Cooke ................ A61B 10/0275 600/567 |
| 2009/0024056 | A1 | 1/2009 | Bacon et al. |
| 2009/0048566 | A1 | 2/2009 | Ferguson et al. |
| 2009/0299220 | A1 * | 12/2009 | Field .................. A61B 10/0275 600/567 |

(Continued)

FOREIGN PATENT DOCUMENTS

EP    0550069 A1    7/1993
JP    2011-177314 A    9/2011

(Continued)

*Primary Examiner* — May A Abouelela
(74) *Attorney, Agent, or Firm* — Park, Kim & Suh, LLC

(57) ABSTRACT

The present invention relates to a needle guide device having a housing, a core needle, a guide needle assembly having a slide or a push button and a spring for biopsy, which is capable of easily separating a guide needle and a core needle.

15 Claims, 18 Drawing Sheets

(56) References Cited

U.S. PATENT DOCUMENTS

| | | | | |
|---|---|---|---|---|
| 2014/0276839 | A1* | 9/2014 | Forman | A61B 17/1622 |
| | | | | 173/2 |
| 2016/0324507 | A1* | 11/2016 | Herget | A61B 10/0266 |
| 2016/0346519 | A1* | 12/2016 | Bagwell | A61B 17/3401 |
| 2017/0238913 | A1* | 8/2017 | Schässburger | A61B 10/0233 |
| 2018/0103939 | A1* | 4/2018 | Van Liere | A61B 10/0275 |
| 2018/0147011 | A1* | 5/2018 | Gilliland | A61B 17/3423 |
| 2018/0153525 | A1* | 6/2018 | Choi | A61B 10/0233 |
| 2018/0153526 | A1* | 6/2018 | Nock | A61B 50/00 |
| 2018/0168682 | A1* | 6/2018 | Hazard, III | A61B 34/20 |
| 2018/0214140 | A1* | 8/2018 | Nock | A61B 90/11 |
| 2018/0242959 | A1* | 8/2018 | Keller | A61B 10/0283 |
| 2018/0249988 | A1* | 9/2018 | Neal | A61B 10/0266 |
| 2020/0397419 | A1* | 12/2020 | Buchanan | A61B 10/0275 |
| 2021/0030404 | A1* | 2/2021 | Van Liere | A61B 17/3403 |
| 2021/0113197 | A1* | 4/2021 | Ben Arie | A61B 17/3496 |
| 2022/0387006 | A1* | 12/2022 | Jensen | A61B 10/0275 |
| 2023/0011601 | A1* | 1/2023 | Girgenti | F16J 15/3236 |

FOREIGN PATENT DOCUMENTS

| | | |
|---|---|---|
| JP | 2012-532708 A | 12/2012 |
| JP | 2018-519972 A | 7/2018 |
| KR | 10-1523662 B1 | 5/2015 |
| KR | 10-1649713 B1 | 8/2016 |
| KR | 10-2017-0082930 A | 7/2017 |
| WO | 2006/020055 A2 | 2/2006 |

* cited by examiner

NEEDLE GUIDE DEVICE FOR BIOPSY

FIELD OF THE INVENTION

The present invention relates to biopsy technology, and more particularly, to a needle guide device for biopsy, which is capable of easily separating a guide needle and a core needle.

BACKGROUND ART

A biopsy is one of histopathological examinations for collecting living cells, tissues, etc. of a patient's lesion site and analyzing and diagnosing samples. Generally, biopsies are performed when a disease such as cancer is suspected and are classified into an excisional biopsy, an incisional biopsy, a percutaneous biopsy, and the like. Examples of a biopsy of a breast lesion include a core needle biopsy for obtaining a part of a tissue or tumor by a biopsy needle, a vacuum-assisted breast biopsy (VABB) for collecting many tissues by a thick biopsy needle and a vacuum, and the like.

In the core needle biopsy, a needle guide device is used to guide a needle of a biopsy device when the needle is inserted into tissue of a lesion site. The needle guide devices include a housing, a guide needle, and a core needle. The housing or a body is configured to be held and used with one hand of an operator. The core needle or a stylet is coupled to the housing to extend from the housing. The guide needle, a coaxial needle, or a sheath includes a passage through which the core needle passes. A tip of the core needle protrudes from a front end of the guide needle to be inserted into tissue. The core needle is fitted into the guide needle, inserted into tissue, and separated from the guide needle. A biopsy needle is inserted into tissue through the passage of the guide needle to collect tissue samples. The contents disclosed in the above patent documents are incorporated herein by reference.

SUMMARY OF THE INVENTION

The present invention is directed to a needle guide device for biopsy, comprising: a housing comprising: a bore provided at a center, an entrance provided at a front of the housing to be connected to the bore, and a slide hole formed in a side of an outer surface to be connected to the bore; a core needle coupled to the housing to extend toward the front of the housing and provided with a tip at a front end to be inserted into tissue; a guide needle assembly comprising: a hub detachably accommodated in the bore of the housing through the entrance and including at a center with the bore through which the core needle passes, and a guide needle coupled to the bore of the hub and including at a center a passage through which the core needle passes; a slide button including at a center a locking hole in which a snap fit is to be locked, and coupled to the slide hole to be movable between a locking position and an unlocking position of the snap fit; and a spring mounted in the bore of the housing to apply an elastic force in a direction in which the hub is pushed out of the bore of the housing.

And the slide hole may be provided in a top surface of the housing in a direction perpendicular to an axial direction and the needle guide device further may comprise a locator plate above the slide hole in the axial direction of the housing to support the slide button, the locator plate being integrally formed with the housing.

And the slide button may comprise a pair of first slide button snap fits provided at intervals to be adjacent to both sides of the locking hole, and configured to be caught on both sides of the locator plate to restrain the slide button from being moved away from the locking position; and a pair of second slide button snap fits provided to be spaced apart from the pair of first slide button snap fits, and configured to be caught on both sides of the locator plate to restrain the slide button from being moved away from the unlocking position.

And the needle guide device may further comprise a guide groove provided on a bottom surface of the slide button to guide the snap fit to the locking hole.

And the spring may comprise a coil spring, and the needle guide device further comprises: a boss which is provided in the bore of the housing and into which the coil spring is fitted; and a plurality of stoppers provided on an outer surface of the boss adjacent to a front end of the boss to restrain the coil spring.

And the needle guide device may further comprise a scale provided on an outer surface of the guide needle in a longitudinal direction; an indicator coupled to the outer surface of the guide needle to move along the outer surface of the guide needle; and a protective tube configured to detachably fitted in the outer surface of the guide needle to accommodate and protect the core needle and the guide needle.

And the present invention is directed to a needle guide device for biopsy may comprise a housing comprising: a bore provided at a center; an entrance provided at a front of the housing to be connected to the bore; an opening being open from the entrance to expose the bore; a push button provided in the opening and displaceable toward the inside of the bore; and a housing snap fit provided in the opening and displaced toward the inside of the bore when the push button is pressed; a core needle coupled to the housing to extend toward the front of the housing and provided with a tip at a front end to be inserted into tissue; a guide needle assembly comprising: a hub detachably accommodated in the bore of the housing through the entrance of the housing, including a locking hole in which the housing snap fit is to be caught and fixed, and including at a center a bore through which the core needle passes; and a guide needle coupled to the bore of the hub and including at a center a passage through which the core needle passes; and a spring mounted in the bore of the housing to apply an elastic force in a direction in which the hub is pushed out of the bore of the housing.

And the opening of the housing, the housing snap fit, the push button, and the locking hole of the hub may be provided on an upper portion or a top surface of the housing or the hub.

And the push button may be connected to an inner side of the opening of the housing to be pressed toward the inside of the bore of the housing in a direction toward the entrance of the housing, and the housing snap fit may be provided in front of the push button to be connected to the push button.

And the housing snap fit may be moved downward into the bore of the housing, together with the push button, when the push button is pressed.

And the spring may comprise a coil spring, and the needle guide device may further comprise a boss which is provided in the bore of the housing and into which the coil spring is fitted; and a plurality of stoppers provided on an outer surface of the boss adjacent to a front end of the boss to restrain the coil spring.

And the needle guide device may further comprise a scale provided on an outer surface of the guide needle in a longitudinal direction; an indicator coupled to the outer surface of the guide needle to move along the outer surface of the guide needle; and a protective tube configured to detachably fitted in the outer surface of the guide needle to accommodate and protect the core needle and the guide needle.

And when the push button is pressed, a locked state between the housing snap fit and the locking hole of the hub are released and the guide needle assembly is separated toward the front of the bore of the housing due to an elastic force provided by the spring.

And the needle guide device may be for use in a core needle biopsy in which a part of tissue or tumor is obtained by a biopsy needle.

DETAILED DESCRIPTION

Figure 1:
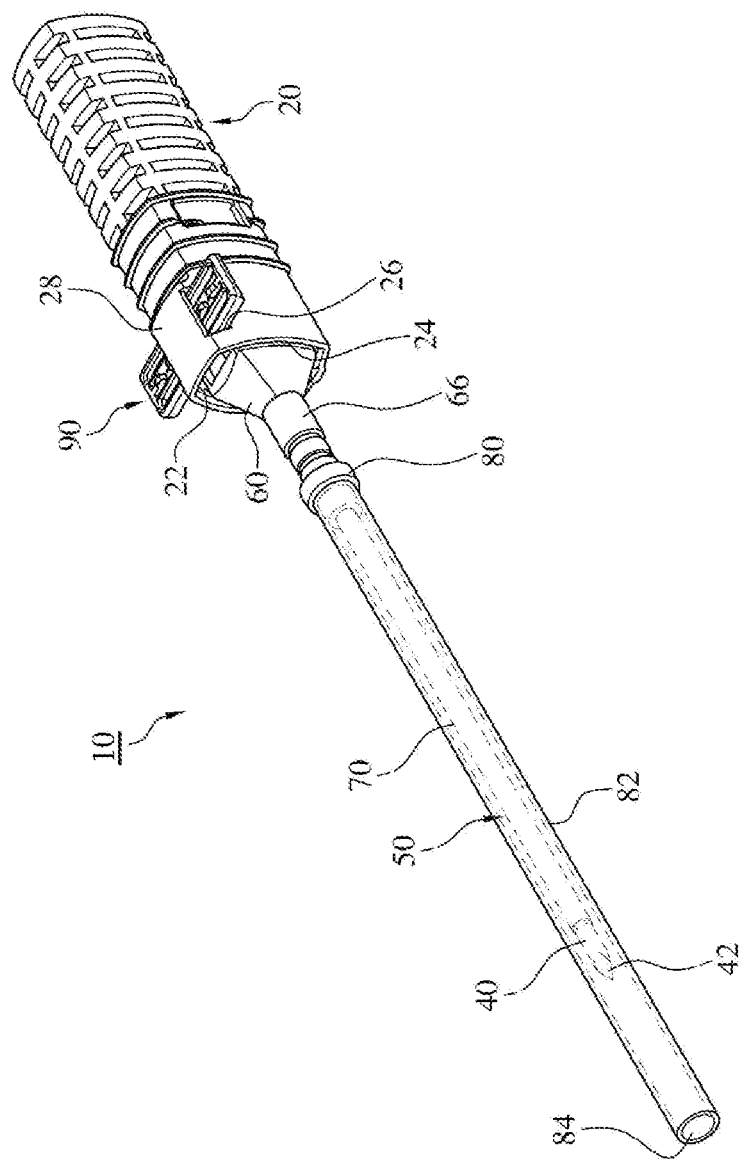
FIG. 1 is a perspective view of a needle guide device for a biopsy according to an embodiment of the present invention.

Hereinafter, exemplary embodiments of the present invention will be described in detail with reference to the accompanying drawings. The present invention is, however, not limited thereto and may be embodied in many different forms. Rather, the embodiments set forth herein are provided so that this disclosure will be thorough and complete, and fully convey the scope of the invention to those of ordinary skill in the art. Throughout the specification, the same reference numbers represent the same elements.

A biopsy needle guide device to be described below may be a biopsy needle guide device for use in a core needle biopsy in which a part of tissue or tumor is obtained with a biopsy needle.

First, referring to FIGS. 1 to 7, a needle guide device 10 for biopsy according to the present invention includes a housing 20. The housing (or a body) 20 is formed of a plastic material so that an operator may hold and use it with one hand. The housing 20 includes a bore 22 formed at a center, an entrance 24 formed at the front of the housing 20 to be connected to the bore 22, and a slide hole 26 formed in an upper surface of the housing 20.

The slide hole (or a guide hole) 26 is formed in the upper surface of the housing 20 in a direction perpendicular to an axial direction. Although the slide hole 26 is illustrated and described as being formed in the upper surface of the housing 20, this is only an example and the slide hole 26 may be formed in an outer surface, e.g., a lateral or bottom surface, of the housing 20. Above the slide hole 26, a locator plate 28 is integrally formed with the housing 20 in the axial direction of the housing 20. A boss 30 protrudes from the bottom of the bore 22. A plurality of stoppers 32 may be formed on an outer circumferential surface near an inner end of the boss 30 to prevent separation of a spring mounted on the boss 30.

The needle guide device 10 for biopsy according to the present invention includes a core needle 40 coupled to the housing 20 to extend long to the front of the housing 20. A rear end of the core needle (or stylet) 40, which is elongated, is coupled to a center of the boss 30. A tip 42 is formed at a front end of the core needle 40 to be inserted into tissue.

The needle guide device 10 for biopsy according to the present invention includes a guide needle assembly 50 detachably coupled to the housing 20. The guide needle assembly 50 includes a hub 60 and a guide needle 70. The hub 60 is detachably accommodated in the bore 22 of the housing 20 and is formed of plastic. The hub 60 includes a bore 62 formed at a center, a sleeve 64 protruding forward to be connected to the bore 62, and a snap fit 66 formed at the top.

The core needle 40 passes through the bore 62 and the sleeve 64 of the hub 60 and extends to the front of the hub 60. The snap fit (or snap hook) 66 is fitted into the slide hole 26 through the bore 62 of the housing 20. Although the snap fit 66 is illustrated and described as being formed at the top of the hub 60, this is only an example and the snap fit 66 may be formed on a side of an outer surface, e.g., a lateral or bottom surface, of the hub 60.

A rear end of the guide needle 70 is coupled to the sleeve 64. The guide needle 70 is provided with a passage (or bore) 72 which the core needle 40 is fitted into and passes through. The tip 42 protrudes from the front end of the guide needle 70. A scale 74 is formed on an outer surface of the guide needle 70 in a longitudinal direction. An operator may identify a depth to which the guide needle 70 is inserted into tissue through the scale 74. Furthermore, an indicator 80 is coupled to an outer surface of the guide needle 70 to move along the guide needle 70. The indicator 80 is formed in a sleeve or cylinder shape.

As illustrated in FIG. 1, a protective tube 82 is fitted in the outer surface of the guide needle 70 to accommodate and protect the core needle 40 and the guide needle 70. The guide needle 70 is detachably fitted into a bore 84 of the protective tube 82. The protective tube 82 is formed of a transparent and flexible synthetic resin material.

Referring to FIGS. 1 to 8, the needle guide device 10 for biopsy according to the present invention includes a slide button 90 coupled to the slide hole 26 to lock the snap fit 66. The slide button 90 is formed of plastic. The slide button 90 is formed in a substantially plate shape coupled to the slide hole 26 to be movable between a locking position P1 and an unlocking position P2 of the snap fit 66. The slide button 90 is elastically supported by the locator plate 28 to be confined in the slide hole 26.

Figure 6:
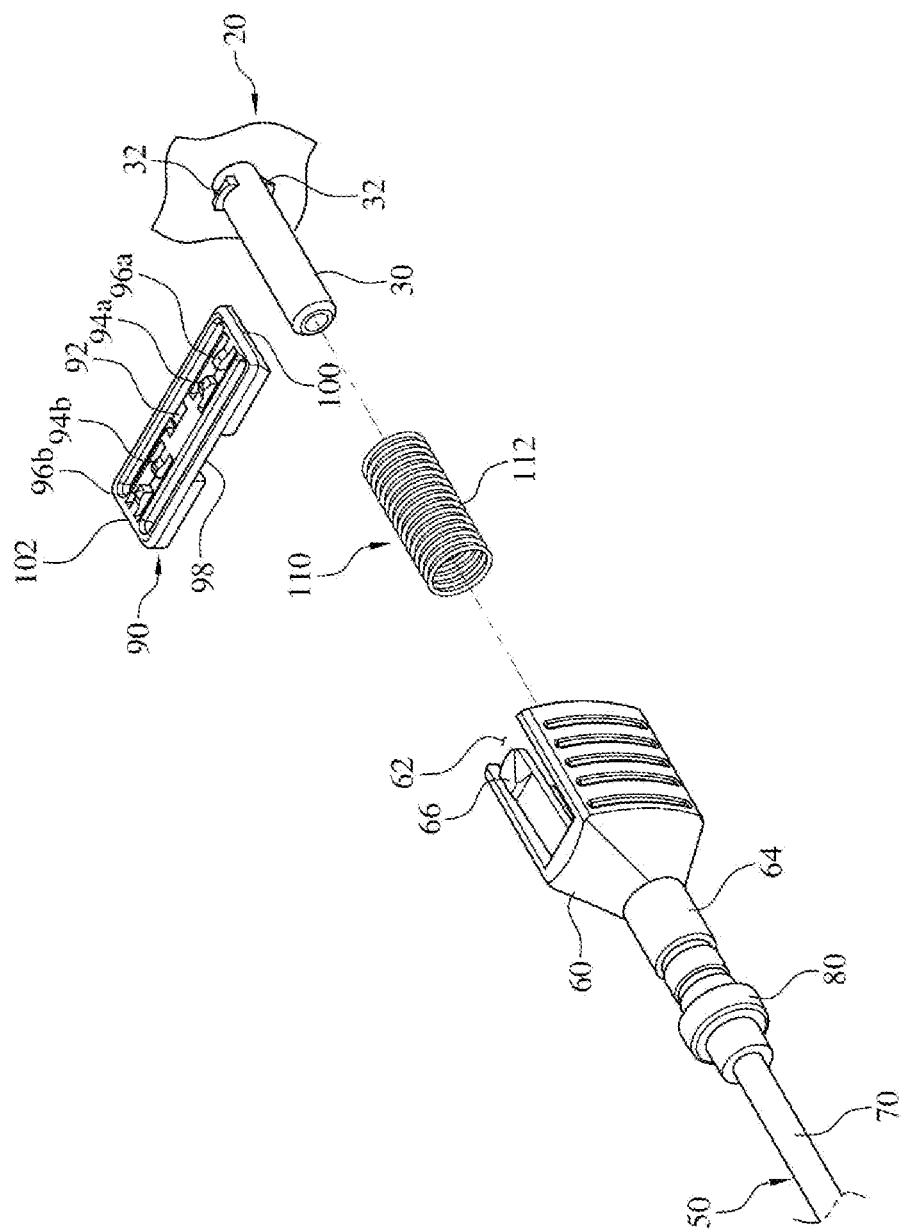
FIG. 6 is a perspective view illustrating a state in which a housing, a guide needle assembly, a slid button, and a spring are separated from a needle guide device for biopsy, according to an embodiment of the present invention.
Figure 8:
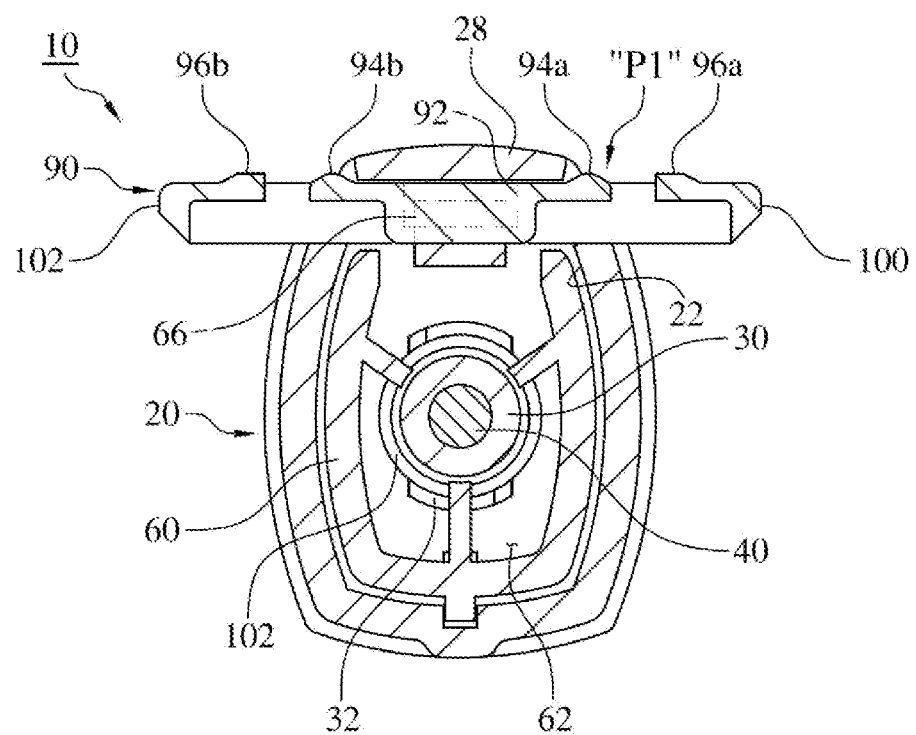
FIG. 8 is a cross-sectional view illustrating a locked state of a slide button of a needle guide device for biopsy, according to an embodiment of the present invention.
Figure 9:
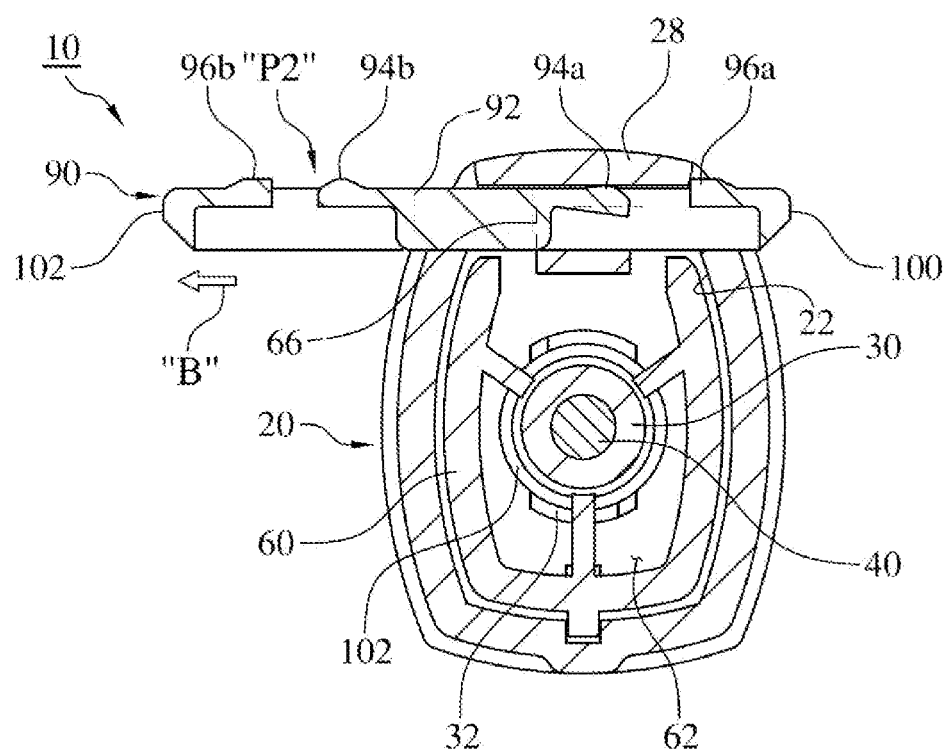
FIG. 9 is a cross-sectional view illustrating an unlocked state of a slide button of a needle guide device for biopsy, according to an embodiment of the present invention.

As clearly shown in FIGS. 6, 8 and 9, the slide button 90 includes a locking hole 92, a pair of first slide button snap fits 94a and 94b, and a pair of second slide button snap fits 96a and 96b. The locking hole 92 is formed in a center of the slide button 90 to lock the snap fit 66 therein. The first slide button snap fits 94a and 94b are formed at intervals on a top surface of the slide button 90 to be adjacent to both sides of the locking hole 92. The first slide button snap fits 94a and 94b are caught on both sides of the locator plate 28, thus blocking the slide button 90 from being separated from the locking position P1. In some embodiments, the first slide button snap fits 94a and 94b may be embodied as a pair of positioning protrusions configured to be caught on the both sides of the locator plate 28 so as to block the slide button 90 from being separated from the locking position P1. The positioning protrusions allow movement of the slide button 90 when elastically deformed.

The second slide button snap fits 96a and 96b are formed on the top surface of the slide button 90 to be respectively spaced apart from the first slide button snap fits 94a and 94b. The second slide button snap fits 96a and 96b are caught on the both sides of the locator plate 28, thus blocking the slide button 90 from being separated from the unlocking position P2. In some embodiments, one of the second slide button snap fits 96a and 96b, e.g., the second slide button snap fit 96b, may be embodied as a stopper formed integrally with the slide button 90. The stopper is caught on one side of the locator plate 28 to restrain the unlocking position P2 of the slide button 90. The slide button 90 is moved in one direction along the slide hole 26 due to the stopper.

The slide button 90 further includes a guide groove 98 to connect the locking hole 92 and a front end of the slide button 90. The snap fit 66 is guided toward the locking hole 92 along the guide groove 98 and is locked in the locking hole 92. The slide button 90 includes a first button portion 100 and a second button portion 102. The first and second button portions 100 and 102 is formed on both sides of the slide button 90. When one of the first and second button portions 100 and 102 is pressed, the slide button 90 is moved from the locking position P1 to the unlocking position P2 along the slide hole 26.

Referring to FIGS. 4 to 7, the needle guide device 10 for biopsy according to the present invention includes a spring 110 for pushing the guide needle assembly 50 out of the bore 22 of the housing 20 when the snap fit 66 is unlocked. The spring 110 includes a coil spring 112 fitted into the boss 30 to apply an elastic force in a direction pushing the hub 60 out of the bore 62. The coil spring 112 is caught by the stoppers 32 to be prevented from being separated from the boss 30. The coil spring 112 may include a coil spring plate, a torsion spring, an elastic body, or the like for applying an elastic force in a direction pushing the hub 60 out of the bore 62.

An operation of a needle guide device for biopsy according to the present invention configured as described above will be described below.

Figure 5:
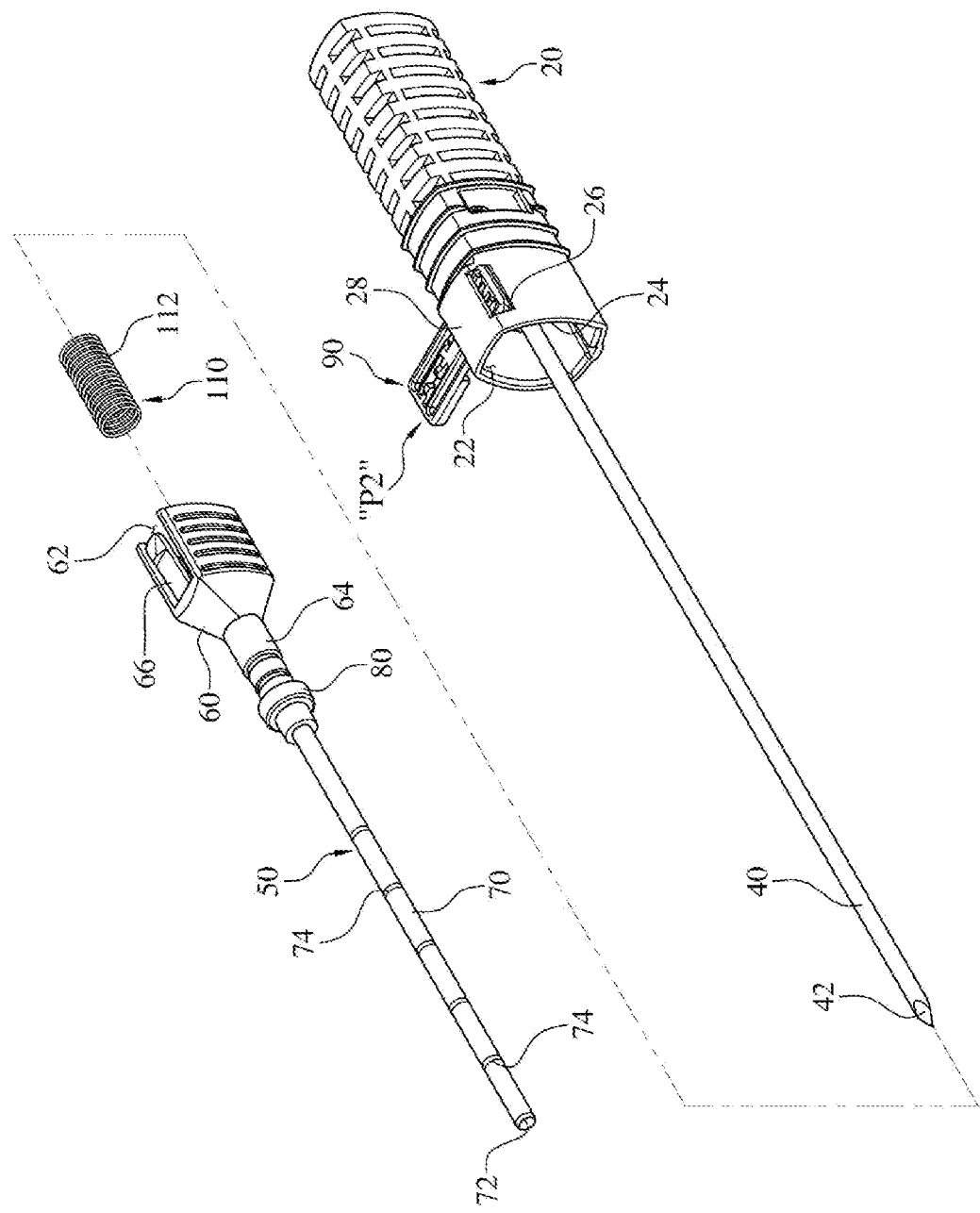
FIG. 5 is a perspective view illustrating a housing, a guide needle assembly, and a spring separated from a needle guide device for biopsy, according to an embodiment of the present invention.
Figure 7:
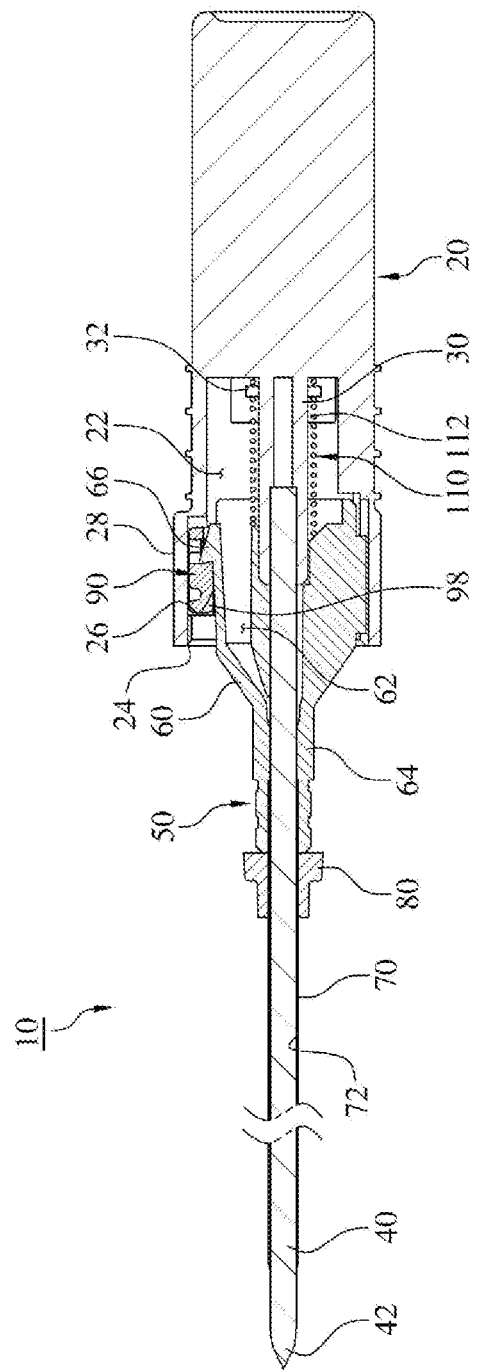
FIG. 7 is a cross-sectional view of a needle guide device for biopsy, according to an embodiment of the present invention.

Referring to FIGS. 5 to 7, when the hub 60 is fitted into the bore 22 of the housing 20 while inserting the core needle 40 into the passage 72 of the guide needle 70, a rear end of the hub 60 is fitted into the bore 22 while pushing and compressing the coil spring 112. The snap fit 66 is elastically deformed and locked in the locking hole 92 along the guide groove 98 while passing the front end of the slide button 90 located at the locking position P1.

Figure 2:
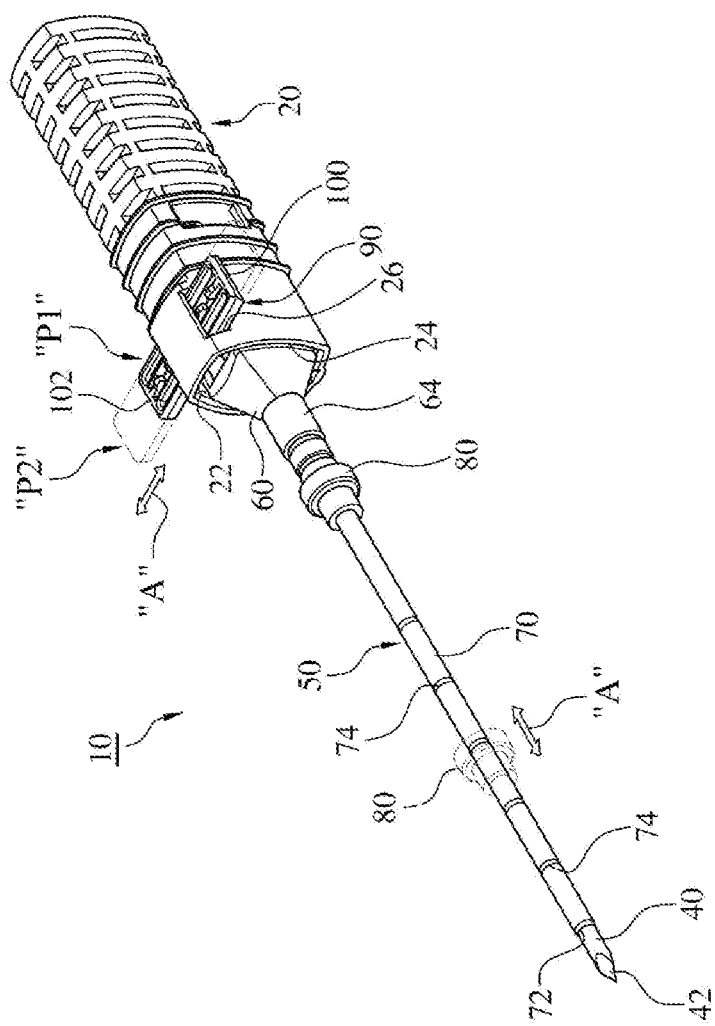
FIG. 2 is a perspective view illustrating a state in which a protective tube is separated from a needle guide device for biopsy, according to an embodiment of the present invention.
Figure 3:
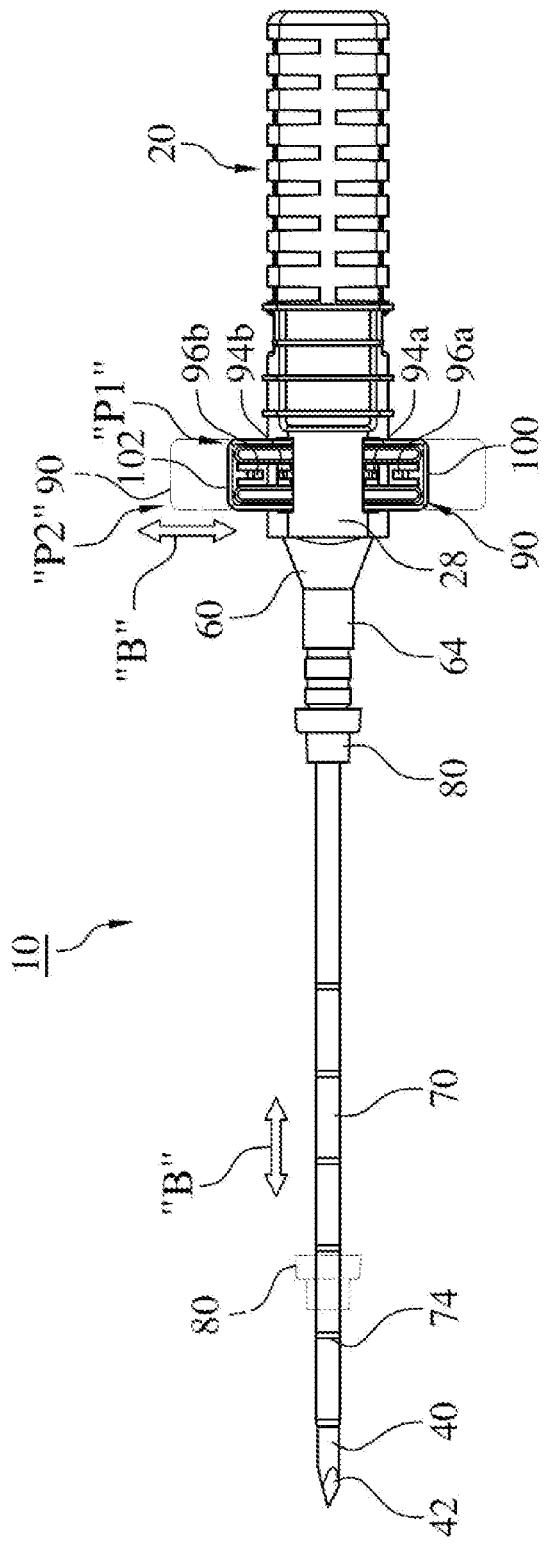
FIG. 3 is a plan view of a needle guide device for a biopsy, according to an embodiment of the present invention.

Referring to FIGS. 2, 3 and 8, each of the first and second slide button snap fits 94a, 94b, 96a, and 96b is elastically deformed while being supported by the locator plate 28 when the slide button 90 is fitted into the slide hole 26, thereby allowing entrance of the slide button 90. As illustrated in FIG. 8, after the slide button 90 is fitted into the slide hole 26, the first and second slide button snap fits 94a and 94b are restored and caught on both sides of the locator plate 28, thereby restraining the locking position P1 of the slide button 90 to prevent the slide button 90 from being separated from the slide hole 26.

As illustrated in FIGS. 1 and 2, after separating the protective tube 82 from the guide needle 70, an operator moves the indicator 80 along the guide needle 70 as indicated by an arrow "A" of FIG. 2. The operator may identify a depth to which the guide needle 70, i.e., the core needle 40, is inserted into tissue through the scale 74 indicated by the indicator 80.

Referring to FIGS. 2, 3, and 9, when the operator inserts the tip 42 of the core needle 40 into the tissue and the tip 42 reaches a tissue sample, the first or second button portion 100 or 102, e.g., the first button portion 100, is pressed to move the slide button 90 from the locking position P1 to the unlocking position P2 as indicated by an arrow "B". As the slide button 90 is operated from the locking position P1 to the unlocking position P2, the snap fit 66 is elastically deformed, released from the locking hole 92, and therefore unlocked. As illustrated in FIG. 9, the second slide button snap fit 96a is caught on one side of the locator plate 28, thereby restraining the slide button 90 to prevent the slide button 90 from being separated from the slide hole 26.

Figure 4:
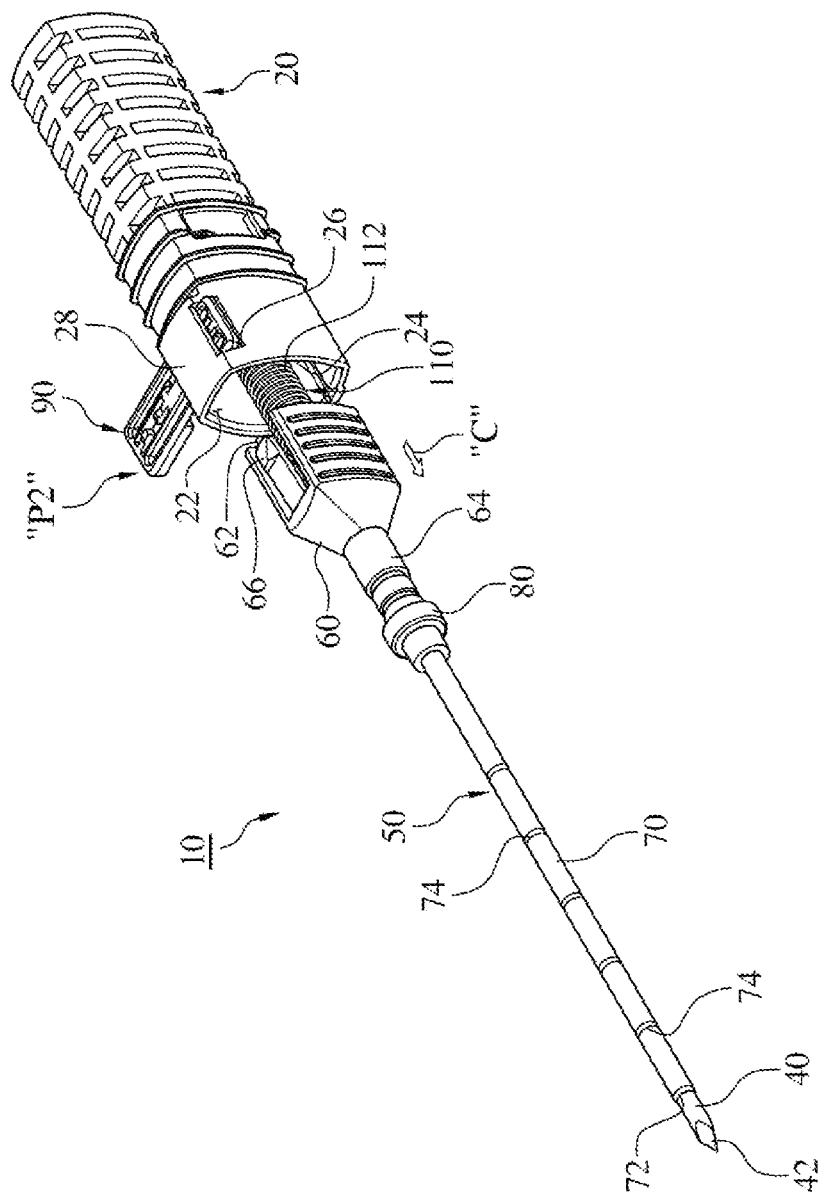
FIG. 4 is a perspective view illustrating a state in which in the needle guide device for biopsy, a housing and a hub of a guide needle assembly are separated by an operation of a slide button, according to an embodiment of the present invention.

Next, when the snap fit 66 is unlocked, the coil spring 112 is restored due to an elastic force and thus the housing 20 is pushed against the hub 60, thereby causing the hub 60 to be separated from the bore 62, as indicated by an arrow "C" of FIG. 4. When the hub 60 is separated from the bore 62, the operator is able to easily separate the core needle 40 from the passage 72 of the guide needle 70 by pulling the housing 20 with one hand. After the guide needle 70 and the core needle 40 are separated from each other, the operator may insert a needle of a biopsy device through the passage 72 of the guide needle 70 to collect a tissue sample. As described above, in the needle guide device 10 according to the present invention, the guide needle 70 and the core needle 40 may be separated from the housing 20 by a one-touch type, thereby increasing efficiency of a biopsy.

The present invention may further provide embodiments of FIGS. 10 to 18, in which the slide button 90 illustrated in FIGS. 1 to 8 is replaced with a push button 90' to further improve operability of a needle guide for biopsy. A description of parts that are the same as those of the embodiments described above with reference to FIGS. 1 to 8 will be omitted here.

Figure 10:
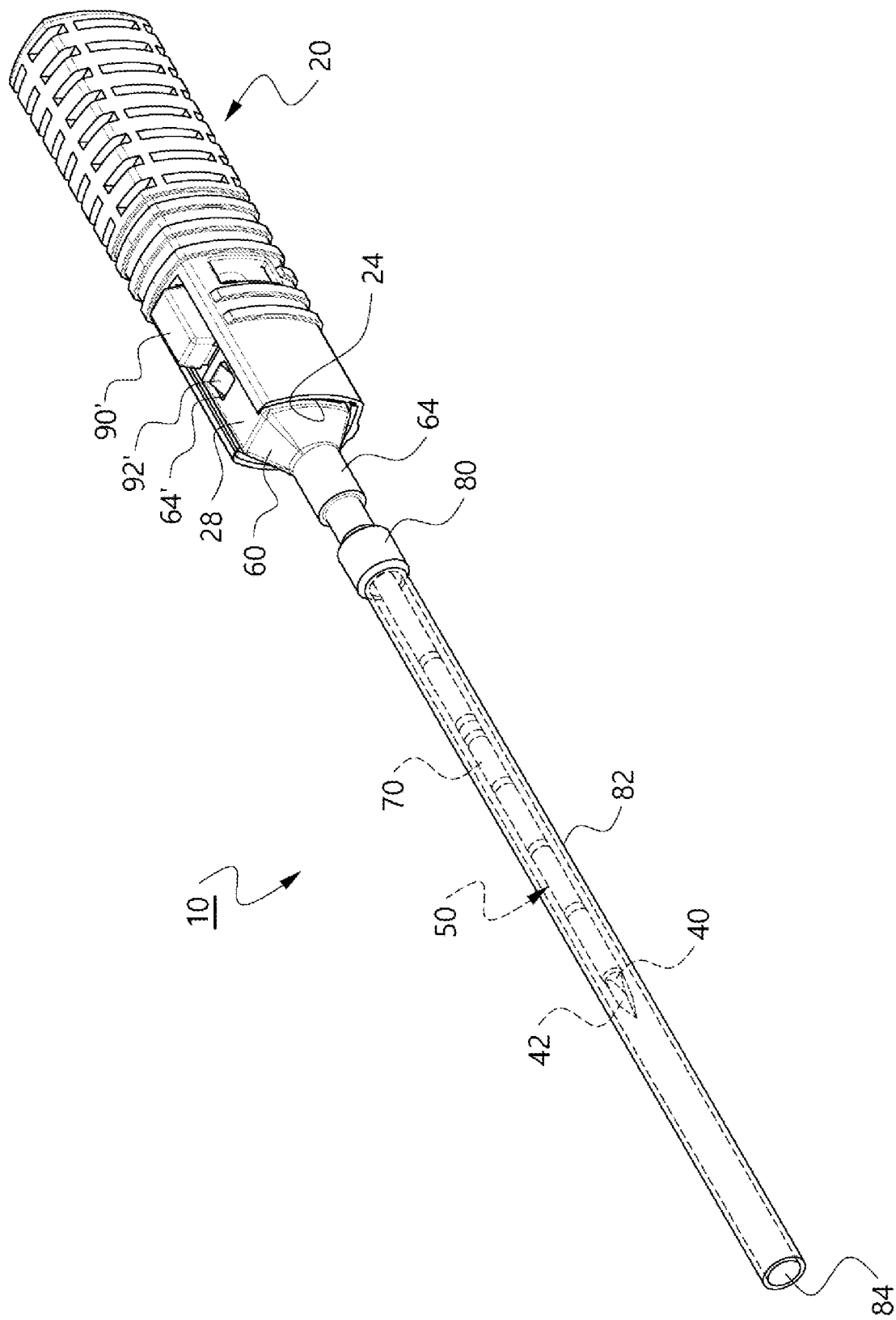
FIG. 10 is a perspective view of a needle guide device for a biopsy, according to another embodiment of the present invention.
Figure 11:
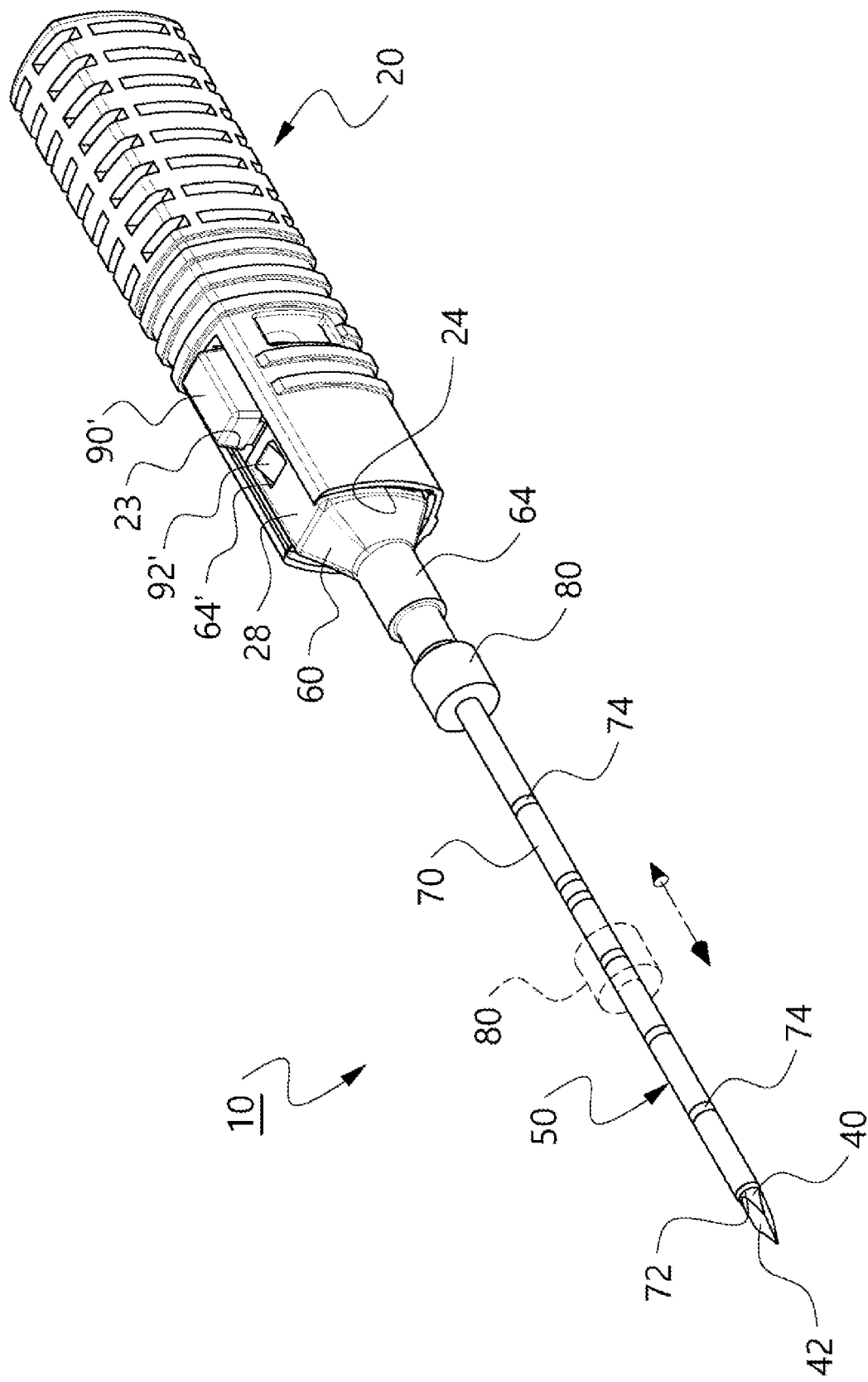
FIG. 11 is a perspective view of a state in which a protective tube is separated from a needle guide device for biopsy, according to another embodiment of the present invention.
Figure 12:
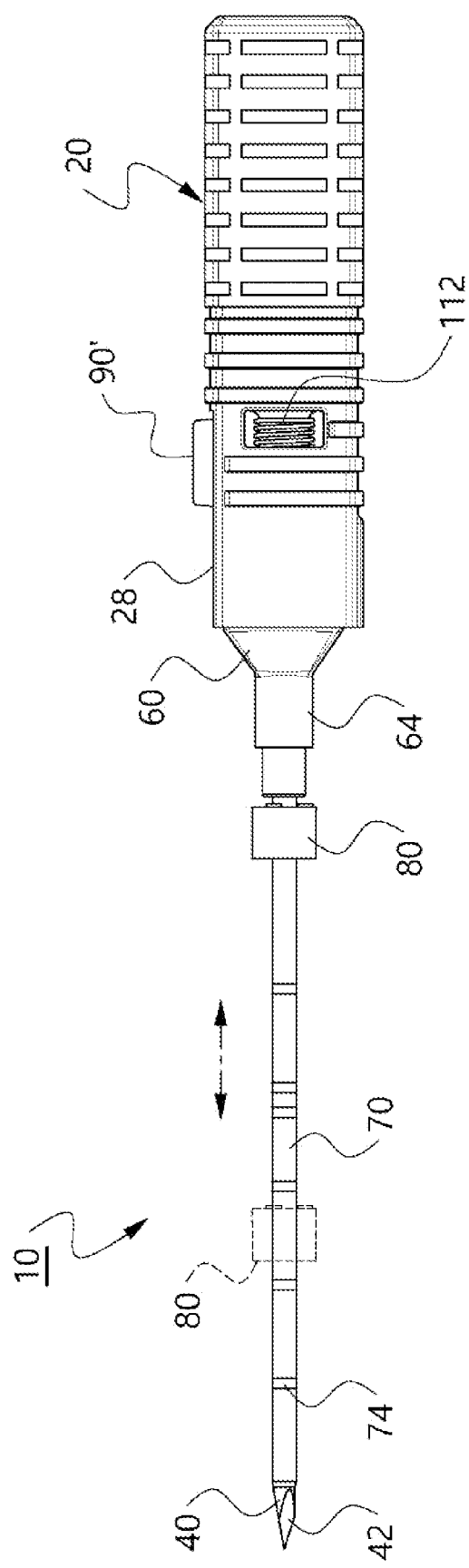
FIG. 12 is a side view of a needle guide device for a biopsy, according to another embodiment of the present invention.
Figure 13:
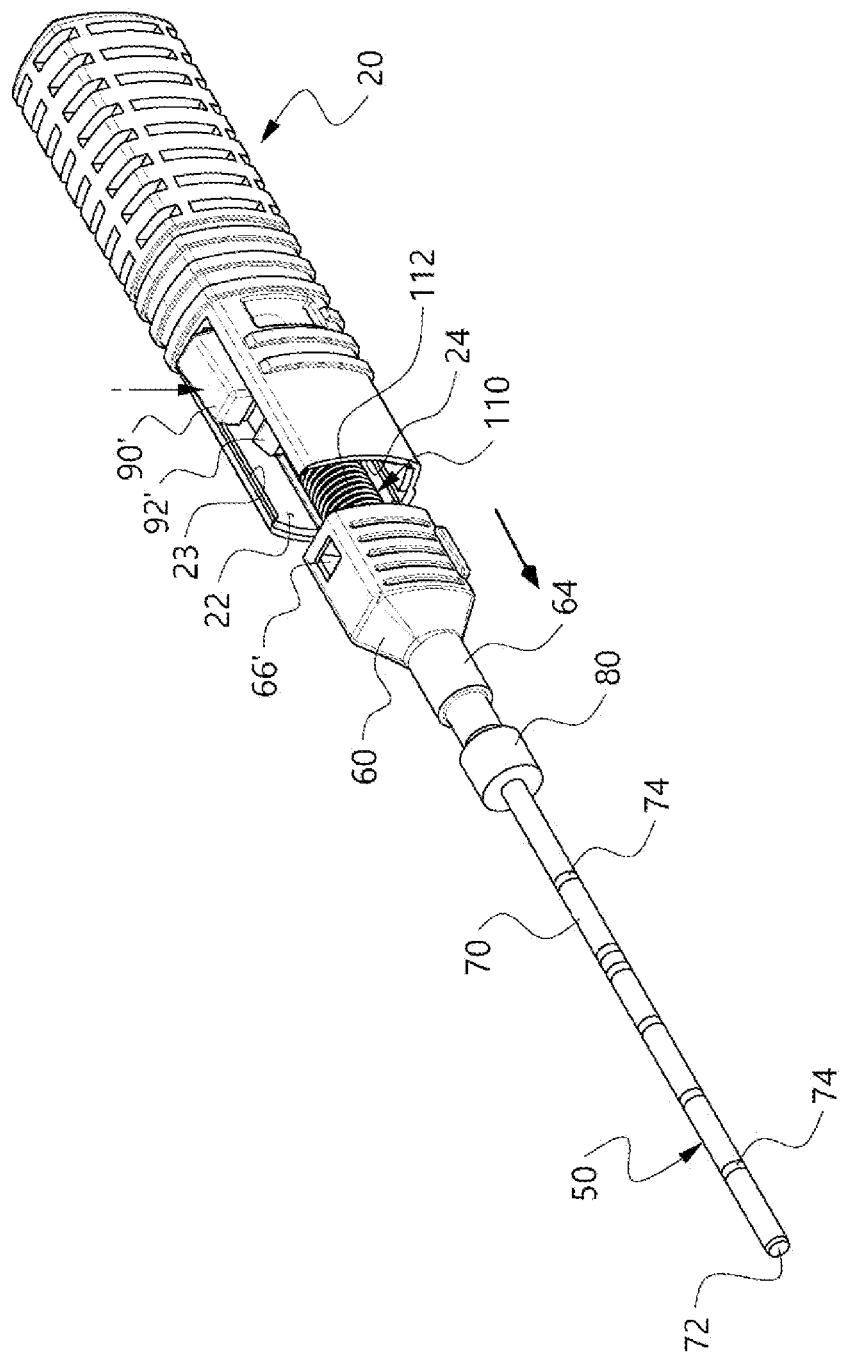
FIG. 13 is a perspective view of a state in which a housing and a hub of a guide needle assembly of a needle guide device for biopsy are separated from each other by an operation of a push button, according to another embodiment of the present invention.
Figure 14:
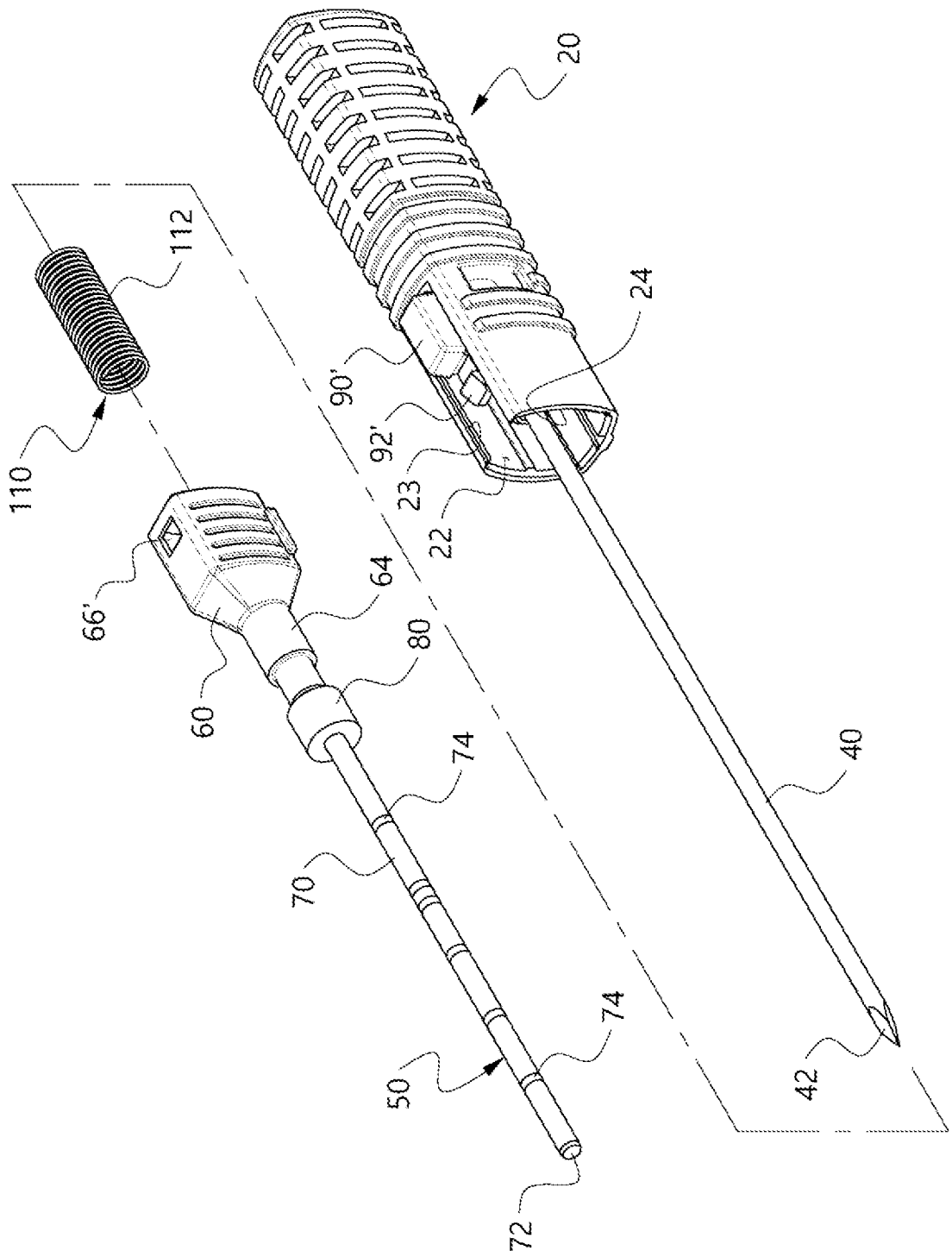
FIG. 14 is a perspective view of a state in which a housing, a guide needle assembly, and a spring of a needle guide device for biopsy are separated, according to another embodiment of the present invention.
Figure 15:
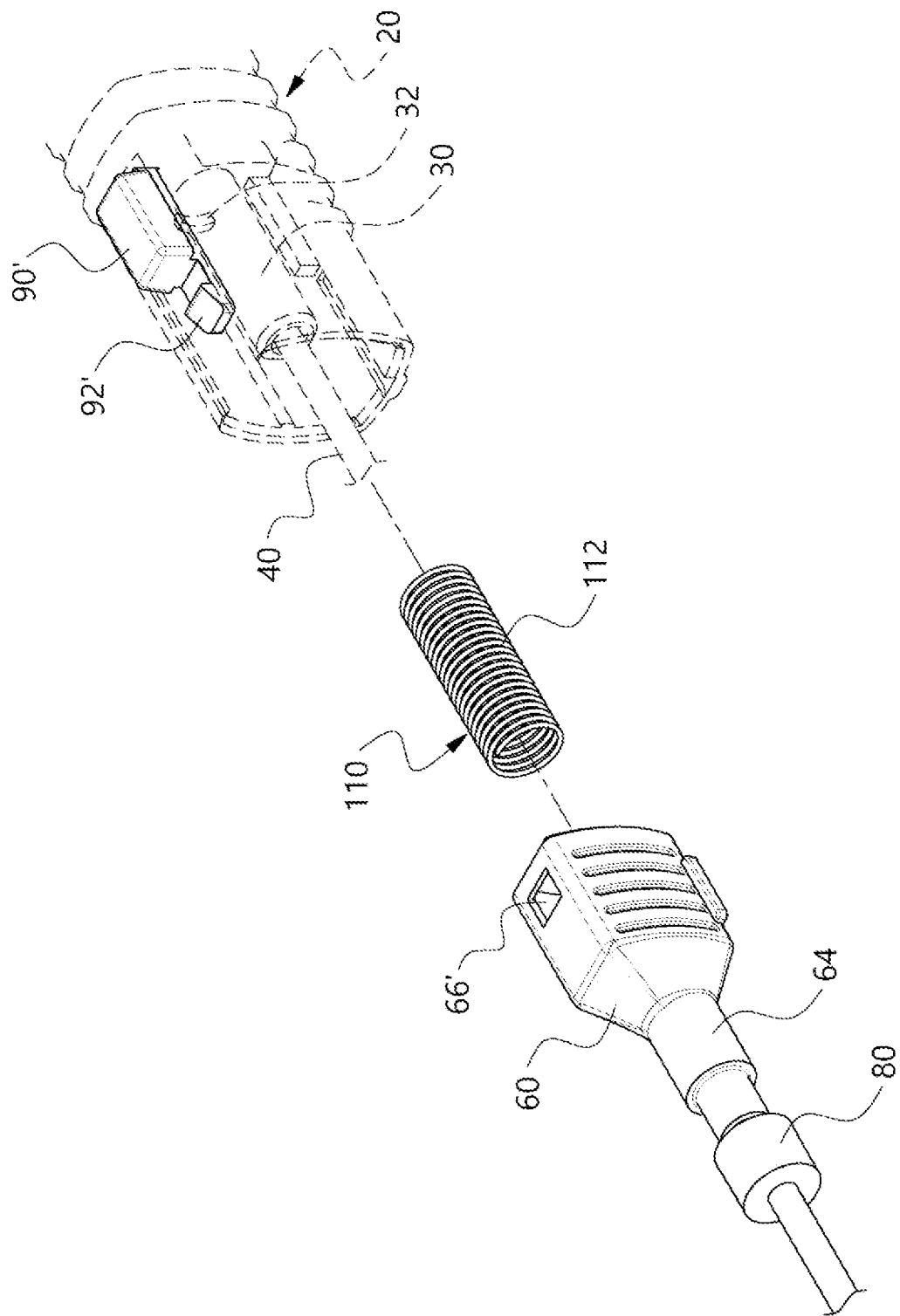
FIG. 15 is a perspective view of a state in which a push button of a housing, a housing snap fit, a guide needle assembly, and a spring of a needle guide device for biopsy are separated, according to another embodiment of the present invention.
Figure 16:
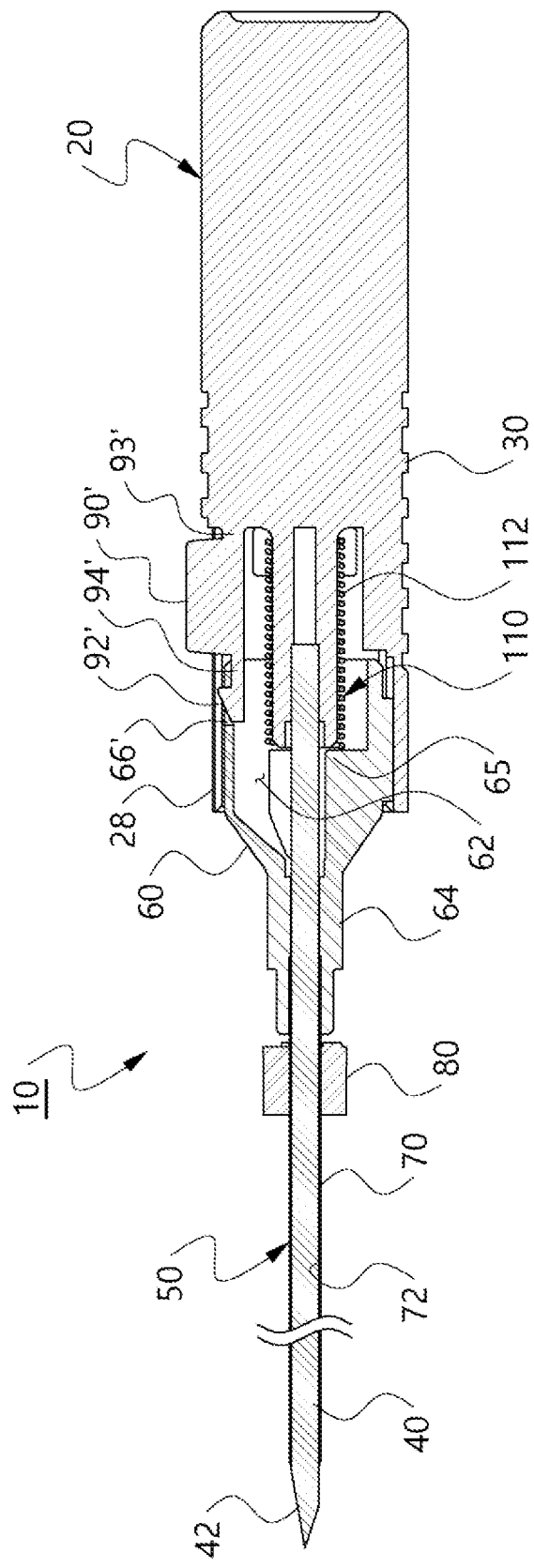
FIG. 16 is a cross-sectional view of a needle guide device for a biopsy, according to another embodiment of the present invention.

FIG. 10 is a perspective view of a needle guide device 10 or a biopsy, according to another embodiment of the present invention. FIG. 11 is a perspective view of a state in which a protective tube is separated from the needle guide device 10 for biopsy, according to another embodiment of the present invention. FIG. 12 is a side view of the needle guide device 10 for a biopsy, according to another embodiment of the present invention. FIG. 13 is a perspective view of a state in which a housing 20 and a hub 60 of a guide needle assembly 50 of the needle guide device 10 for biopsy are separated from each other by an operation of a push button 90', according to another embodiment of the present invention. FIG. 14 is a perspective view of a state in which the housing 20, the guide needle assembly 50, and a spring 110 of the needle guide device 10 for biopsy are separated, according to another embodiment of the present invention. FIG. 15 is a perspective view of a state in which the push button 90' of the housing 20, a housing snap fit 92', the guide needle assembly 50, and the spring 110 of the needle guide device 10 for biopsy are separated, according to another embodiment of the present invention. FIG. 16 is a cross-sectional view of a needle guide device 10 for a biopsy, according to another embodiment of the present invention.

The needle guide device 10 for biopsy according to the embodiments of FIGS. 10 to 17 may include a housing 20 including a bore 22 formed at a center, an entrance 24 formed at the front of the housing 20 to be connected to the bore 22, an opening 23 being open from the entrance 24 to expose the bore 22, a push button 90' connected to an inner side of the opening 23 and displaced toward the inside of the bore 22 when pushed, the housing snap fit 92' connected to the front of the push button 90' and displaced toward the inside of the bore 22 when the push button 90' is pushed; a core needle 40 coupled to the housing 20 to extend to the front of the housing 20, and provided with a tip at a front end thereof to be inserted into tissue; a guide needle assembly 50 including a hub 60, which is detachably accommodated in the bore 22 of the housing 20 through the entrance 24 of the housing 20 and provided with a locking hole 66' in which the housing snap fit 92' is to be hooked and fixed, and in which the bore 22 through which the core needle 40 passes is provided at a center, and a guide needle 70 coupled to a bore 62 of the hub 60 and including at a center a passage through which the core needle 40 passes; and a spring 110 mounted in the bore 22 of the housing 20 to apply an elastic force in a direction pushing the hub 60 out of the bore 22 of the housing 20.

Similarly, the housing (or body) 20 of the needle guide device 10 for biopsy of FIGS. 10 to 17 may be held and used with one hand of an operator, formed of plastic, and provided with a number of irregularities or the like to prevent slipping.

Similarly, the biopsy needle guide device 10 of FIGS. 10 to 17 may include a core needle 40 and a guide needle assembly 50, which are coupled to the housing 20, and the guide needle assembly 50 may include a hub 60, which is separable from the bore 22 of the housing 20 and includes a bore 62 therein and a sleeve 64 at a front end, and a guide needle 70, the rear end of which is coupled to the sleeve 64.

A tip 42 of the core needle 40 protrudes from a front end of the guide needle 70 while passing through the guide needle 70, and a scale 74, an indicator 80 moving along the guide needle 70, and a protective tube 82 may be provided on an outer surface of the guide needle 70.

However, unlike the above-described embodiments, as illustrated in FIGS. 13 to 15, the needle guide device 10 for biopsy may include the bore 22 formed at the center of the housing 20, the entrance 24 formed at the front of the housing 20 to be connected to the bore 22, and the opening 23, which is open from the entrance 24 and is open upward.

Accordingly, the locator plate of the above-described embodiments may be omitted, and a housing snap fit 92' and the push button 90', which will be described below, may be provided backward on the opening 23.

In the embodiments described above with reference to FIGS. 1 to 8, the slide button is configured separately from the housing 20, thus increasing the number of components, and slides in left and right directions and thus may be difficult to be handled with one hand. Accordingly, in the embodiment of FIGS. 10 to 17, the push button 90' is applied instead of a slide button.

The push button 90' may be formed integrally with the housing 20 rather than being separately configured from the housing 20 or the hub 60.

In order to integrally form the push button 90' with the housing 20, the housing 20 includes a bore 22 formed at a center and an entrance 24 formed at the front of the housing 20 to be connected to the bore 22 but may include an opening 23, which is open to communicate with the entrance 24 so as to expose the bore 22, at a front side, a push button 90' connected to an inner side of the opening 23 and displaced toward the inside of the bore 22 when pressed, and a housing snap fit 92' connected to the front of the push button 90' and displaced toward the inside of the bore 22 when the push button 90' is pressed.

As illustrated in FIGS. 13 and 14, the opening 23 of the housing 20 refers to a region located at the front of the housing 20 to communicate with the entrance 24, thus exposing the bore 22 inside the housing 20.

In the embodiments of FIGS. 10 to 17, the push button 90' and the housing snap fit 92' are provided on an upper portion of the housing 20 and thus the opening 23 for forming the push button 90' and the housing snap fit 92' may also be provided above the entrance 24 of the housing 20 to be open from the entrance 24.

Therefore, when an operator performs a task while holding the housing 20 with one hand, it is convenient to handle the housing 20 with a thumb and thus the push button 90' and the housing snap fit 92' are illustrated as being provided on the upper portion of the housing 20. However, the push button 90' and the housing snap fit 92' may be provided on a side, a lower portion or a bottom surface of the housing 20 and the opening 23 may be formed at the side, the lower portion, or the bottom surface of the housing 20. Thus, in the following description, that the push button 90' or the housing snap fit 92' protrudes or is exposed upward should be interpreted as only one embodiment.

The push button 90' and the housing snap fit 92' may be integrally formed with the housing 20, an inner side of the opening 23 of the housing 20 and the push button 90' may be connected through a first connection part 93' (see FIG. 17), the push button 90' and the housing snap fit 92' may be connected through a second connection part 94' (see FIG. 17), and the housing 20 may be formed of a plastic material having a certain degree of flexibility. Thus, when the push button 90' is pressed, the first connection part 93' is not broken but is bent, and thus, the push button 90' is moved inside the bore 22 of the housing 20, and the housing snap fit 92' connected to the push button 90' through the second connection part 94' is moved downward together with the push button 90' and thus be separated from a locking hole 66' of the hub 60 to be in an unlocked state.

Therefore, the push button 90' may be formed integrally with the inner side of the opening 23 of the housing 20 to be pressed toward the entrance 24 of the housing 20, i.e., the inside of the bore 22 of the housing 20, and the housing snap fit 92' may be formed integrally with the housing 20 and the push button 90'.

Accordingly, the push button 90' and the housing snap fit 92' may be integrally formed with the housing 20, and the housing snap fit 92' may be configured to be moved downward with the push button 90' when the push button 90' is pressed.

In order to selectively fasten the housing 20 and the hub 60 through the push button 90', the hub 60 may be detachably accommodated in the bore 22 of the housing 20 through the entrance 24 of the housing 20, and a locking hole 66' may be provided through which the housing snap fit 92' may be caught and fixed. The locking hole 66' may be provided on an upper portion or upper surface of the hub 60.

A position of the locking hole 66' may be a position at which when the hub 60 is mounted on the housing 20, a snap fit 92' is caught on a rear end of the locking hole 66' in a state in which the push button 90' is not pressed.

As in the above-described embodiment, the bore 22 through which the core needle 40 passes may be provided at a center of the hub 60.

Similarly, in the embodiment of FIGS. 10 to 17, a spring 110 may be provided in the boss 30 in the form of a coil spring, a torsion spring, an elastic body or the like to provide an elastic force for pushing the guide needle assembly 50 out of the bore 22 of the housing 20 when the housing snap fit 92' is unlocked, and as illustrated in FIG. 15, a boss 30 may be provided to protrude from an inner side of the bore 22 of the housing 20 so as to mount a spring inside the bore 22 of the housing 20. As in the above-described embodiment, a plurality of stoppers 32 may be provided on an outer circumferential surface near an inner side of the boss 30 to prevent the spring 110 from being separated.

As illustrated in FIG. 16, when the hub 60 of the guide needle assembly 50 is mounted on the housing 20, the push button 90' may be in a non-pressed state and the housing snap fit 92' formed integrally with the front of the push button 90' may be locked in the locking hole 66' of the hub 60, so that the needle assembly 50 may be kept fastened with the housing 20. In this case, the spring 110 mounted on the boss of the bore 22 of the housing 20 is maintained in a compressed state while elastically supporting a support part 65 inside the hub 60.

Figure 17:
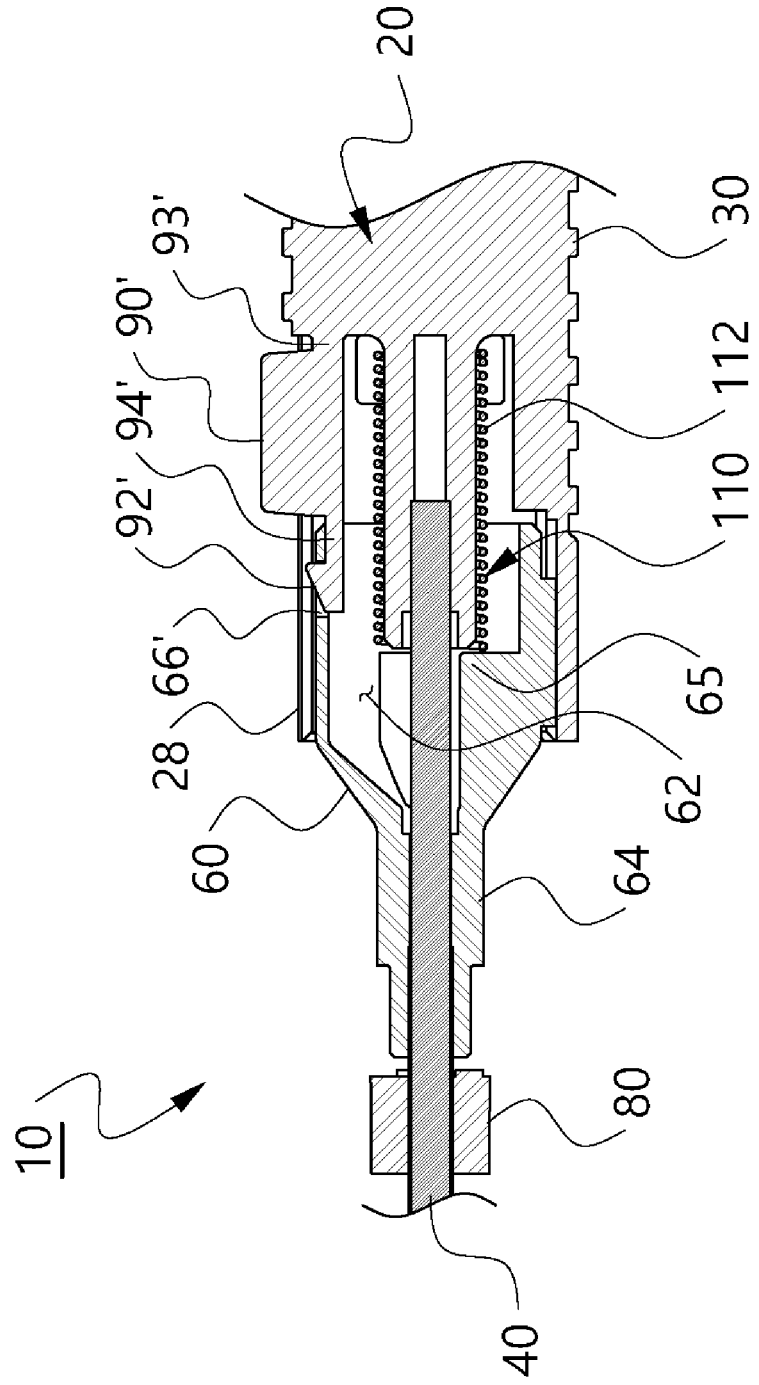
FIG. 17 is a cross-sectional view illustrating a locked state of a slide button of a needle guide device for biopsy, according to another embodiment of the present invention.

FIG. 17 is a cross-sectional view illustrating a locked state of a slide button 10 of a needle guide device for biopsy, according to another embodiment of the present invention.

Figure 18:
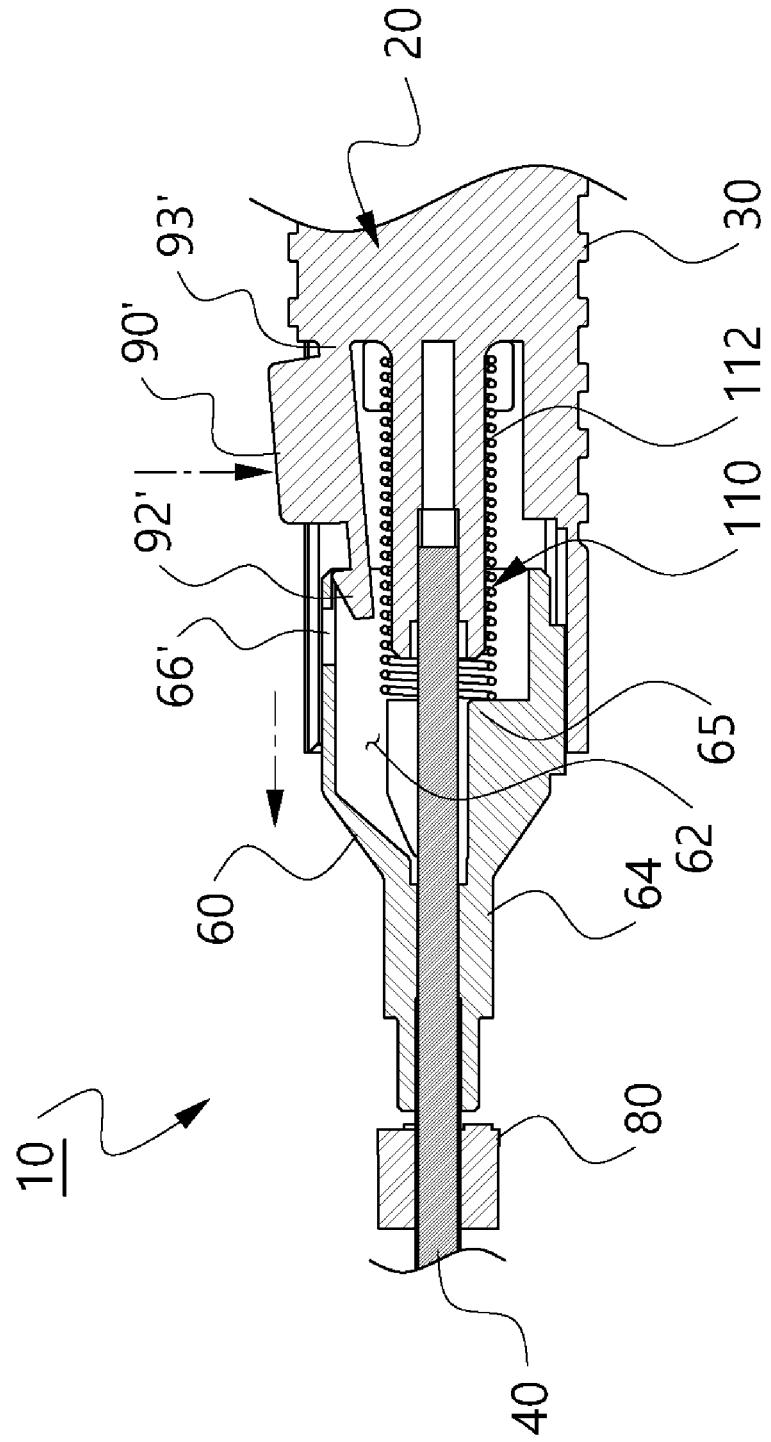
FIG. 18 is a cross-sectional view illustrating an unlocked state of a slide button of a needle guide device for biopsy, according to another embodiment of the present invention.

FIG. 18 is a cross-sectional view illustrating an unlocked state of the slide button of the needle guide device 10 for biopsy, according to another embodiment of the present invention.

As illustrated in FIG. 17, in order to separate a guide needle assembly 50, when an operator presses a push button 90' with the thumb of a hand holding a housing 20 of the needle guide device 10, a housing snap fit 92' in front of the push button 90' may descend and a locked state between the housing snap fit 92' and a locking hole 66' of a hub 60 may be released, thereby unlocking the housing snap fit 92' and the locking hole 66' from each other, as illustrated in FIG. 18.

As described above, the push button 90' and the housing snap fit 92' may be formed integrally with the housing 20, an inner side of an opening 23 of the housing 20 and the push button 90' may be connected through a first connection part 92', the push button 90' and the housing snap fit 92' may be connected through a second connection part 94', and the housing 20 may be formed of a plastic material having a certain degree of flexibility. Thus, the first connection part 92' is not broken but is bent when the push button 90' is pressed, and thus, the push button 90' may be moved inside the bore 22 of the housing 20 and the housing snap fit 92' connected to the push button 90' through the second connection part 94' may be moved downward together with the push button 90' to be released from the locking hole 66', thereby unlocking the housing snap fit 92'.

Therefore, a spring 110 mounted in a compressed state on the boss of the bore 22 of the housing 20 pushes a support part 65 inside the bore 62 of the hub 60 to separate the needle assembly 50 from the front of the housing 20.

Therefore, when the hub 60 of the guide needle assembly 50 is separated from the bore 22 of the housing 20, the operator may easily separate a core needle 40 from a passage 72 of the guide needle 70 by pulling the housing 20 with one hand. After the guide needle 70 and the core needle 40 are separated, the operator may collect a tissue sample by inserting a needle (not shown) of a biopsy device through the passage 72 of the guide needle 70.

As described above, in the needle guide device 10 according to the present invention, the housing 20 to which the guide needle 70 and the core needle 40 are coupled can be easily separated by a one-touch method, thereby increasing efficiency of a biopsy, similar to the above-described embodiment.

However, although as in the above-described embodiment, the guide needle assembly 50 may be separated while holding the needle guide device 10 for biopsy with one hand of an operator, the workability of the push button 90' may be better than that of a slide button in terms of the structure of a thumb, a possibility of loss when the slide button is removed may be reduced, and an effect of reducing the number of components of the needle guide device for biopsy may be achieved.

In a needle guide device for biopsy according to the present invention, a snap fit of a guide needle assembly is configured to be locked or unlocked by a slide button or a push button operated by a one-touch method and thus a guide needle and a core needle can be easily separated. Therefore, the convenience of an operator in using the needle guide for biopsy can be improved, thereby greatly increasing the efficiency of a biopsy. In particular, because the operator can separate the core needle by operating the slide button by a one-touch method with one hand holding a housing, the operator can freely use hands, thereby improving speed and accuracy.

In addition, in an embodiment of according to the present invention in which a needle guide device for biopsy employs a push button, workability can be further improved in consideration of the joint structure of a thumb, and there is no possibility of loss of the push button formed integrally with the housing, and the number of components of the needle guide device for biopsy needle can be reduced.

The above-described embodiments are only exemplary embodiments of the present invention, the scope of the present invention is not limited thereto, various changes, modifications or substitutions may be made by those of ordinary skill in the art within the spirit and claims of the present invention, and such embodiments should be understood to be within the scope of the present invention.

What is claimed is:

1. A needle guide device for biopsy, comprising:
    a housing comprising:
        a bore provided at a center; an entrance provided at a front of the housing to be connected to the bore;
        an opening being open from the entrance to expose the bore;
        a push button provided in the opening and displaceable toward an inside of the bore; and
        a housing snap fit provided in the opening and displaced toward the inside of the bore when the push button is pressed;
    a core needle coupled to the housing to extend toward the front of the housing and provided with a tip at a front end configured to be inserted into tissue;
    a guide needle assembly comprising: a hub detachably accommodated in the bore of the housing through the entrance of the housing, including a locking hole in which the housing snap fit is to be caught and fixed, and including at a center a bore through which the core needle passes; and a guide needle coupled to the bore of the hub and including at a center a passage through which the core needle passes; and
    a spring mounted in the bore of the housing to apply an elastic force in a direction in which the hub is pushed out of the bore of the housing,
    wherein the opening of the housing, the housing snap fit, the push button, and the locking hole of the hub are provided on an upper portion or a top surface of the housing or the hub,
    wherein the housing snap fit is moved downward into the bore of the housing, together with the push button, when the push button is pressed.

2. The needle guide device of claim 1, wherein the push button is connected to an inner side of the opening of the housing to be pressed toward the inside of the bore of the housing in a direction toward the entrance of the housing, and
    the housing snap fit is provided in front of the push button to be connected to the push button.

3. The needle guide device of claim 1, wherein
    the spring comprises a coil spring, and
    the needle guide device further comprises:
        a boss which is provided in the bore of the housing and into which the coil spring is fitted; and
        a plurality of stoppers provided on an outer surface of the boss adjacent to a front end of the boss to restrain the coil spring.

4. The needle guide device of claim 1, further comprising:
    a scale provided on an outer surface of the guide needle in a longitudinal direction;
    an indicator coupled to the outer surface of the guide needle to move along the outer surface of the guide needle; and
    a protective tube configured to detachably fitted in the outer surface of the guide needle to accommodate and protect the core needle and the guide needle.

5. The needle guide device of claim 1, wherein, when the push button is pressed, a locked state between the housing snap fit and the locking hole of the hub is released and the guide needle assembly is separated toward the front of the bore of the housing due to an elastic force provided by the spring.

6. The needle guide device of claim 1, wherein the needle guide device is for use in a core needle biopsy in which a part of tissue or tumor is obtained by a biopsy needle.

7. A needle guide device for biopsy, comprising:
    a housing comprising:
        a bore provided at a center; an entrance provided at a front of the housing to be connected to the bore;
        an opening being open from the entrance to expose the bore;
        a push button provided in the opening and displaceable toward an inside of the bore; and
        a housing snap fit provided in the opening and displaced toward the inside of the bore when the push button is pressed;
    a core needle coupled to the housing to extend toward the front of the housing and provided with a tip at a front end configured to be inserted into tissue;
    a guide needle assembly comprising: a hub detachably accommodated in the bore of the housing through the entrance of the housing, including a locking hole in which the housing snap fit is to be caught and fixed, and including at a center a bore through which the core needle passes; and a guide needle coupled to the bore of the hub and including at a center a passage through which the core needle passes;
    a spring mounted in the bore of the housing to apply an elastic force in a direction in which the hub is pushed out of the bore of the housing;
    a scale provided on an outer surface of the guide needle in a longitudinal direction;
    an indicator coupled to the outer surface of the guide needle to move along the outer surface of the guide needle; and
    a protective tube configured to detachably fitted in the outer surface of the guide needle to accommodate and protect the core needle and the guide needle.

8. The needle guide device of claim 7, wherein the push button is connected to an inner side of the opening of the housing to be pressed toward the inside of the bore of the housing in a direction toward the entrance of the housing, and
    the housing snap fit is provided in front of the push button to be connected to the push button.

9. The needle guide device of claim 7, wherein
    the spring comprises a coil spring, and
    the needle guide device further comprises:
        a boss which is provided in the bore of the housing and into which the coil spring is fitted; and
        a plurality of stoppers provided on an outer surface of the boss adjacent to a front end of the boss to restrain the coil spring.

10. The needle guide device of claim 7, wherein, when the push button is pressed, a locked state between the housing snap fit and the locking hole of the hub is released and the guide needle assembly is separated toward the front of the bore of the housing due to an elastic force provided by the spring.

11. The needle guide device of claim 7, wherein the needle guide device is for use in a core needle biopsy in which a part of tissue or tumor is obtained by a biopsy needle.

12. A needle guide device for biopsy, comprising:
a housing comprising:
  a bore provided at a center; an entrance provided at a front of the housing to be connected to the bore;
  an opening being open from the entrance to expose the bore;
  a push button provided in the opening and displaceable toward an inside of the bore; and
  a housing snap fit provided in the opening and displaced toward the inside of the bore when the push button is pressed;
a core needle coupled to the housing to extend toward the front of the housing and provided with a tip at a front end configured to be inserted into tissue;
a guide needle assembly comprising: a hub detachably accommodated in the bore of the housing through the entrance of the housing, including a locking hole in which the housing snap fit is to be caught and fixed, and including at a center a bore through which the core needle passes; and a guide needle coupled to the bore of the hub and including at a center a passage through which the core needle passes; and
a spring mounted in the bore of the housing to apply an elastic force in a direction in which the hub is pushed out of the bore of the housing,
wherein, when the push button is pressed, a locked state between the housing snap fit and the locking hole of the hub is released and the guide needle assembly is separated toward the front of the bore of the housing due to an elastic force provided by the spring.

13. The needle guide device of claim 12, wherein the push button is connected to an inner side of the opening of the housing to be pressed toward the inside of the bore of the housing in a direction toward the entrance of the housing, and
the housing snap fit is provided in front of the push button to be connected to the push button.

14. The needle guide device of claim 12, wherein
the spring comprises a coil spring, and
the needle guide device further comprises:
  a boss which is provided in the bore of the housing and into which the coil spring is fitted; and
  a plurality of stoppers provided on an outer surface of the boss adjacent to a front end of the boss to restrain the coil spring.

15. The needle guide device of claim 12, wherein the needle guide device is for use in a core needle biopsy in which a part of tissue or tumor is obtained by a biopsy needle.

* * * * *